US00PP32786P2

(12) United States Plant Patent
Rushing

(10) Patent No.: US PP32,786 P2
(45) Date of Patent: Feb. 2, 2021

(54) ***RHAPHIOLEPIS* PLANT NAMED 'DB-01'**

(50) Latin Name: *Rhaphiolepis indica*
Varietal Denomination: DB-01

(71) Applicant: Ralph C Rushing, Semmes, AL (US)

(72) Inventor: Ralph C Rushing, Semmes, AL (US)

(73) Assignee: PLANT DEVELOPMENT SERVICES INC, Loxley, AL (US)

( * ) Notice: Subject to any disclaimer, the term of this patent is extended or adjusted under 35 U.S.C. 154(b) by 0 days.

(21) Appl. No.: 16/873,263

(22) Filed: Mar. 5, 2020

(51) Int. Cl.
*A01H 5/02* (2018.01)
*A01H 6/74* (2018.01)

(52) U.S. Cl.
USPC ..... Plt./254
CPC ..... *A01H 6/74* (2018.05)

(58) Field of Classification Search
USPC ..... Plt./254
CPC ..... A01H 5/02
See application file for complete search history.

*Primary Examiner* — Kent L Bell
(74) *Attorney, Agent, or Firm* — Cassandra Bright

(57) ABSTRACT

A new and distinctive *Rhaphiolepis indica* plant, characterized by its compact, mounding form, unique branching structure, and white flowers flushed with pink at first opening. Plants grow wider than tall, are drought tolerant, and do not require pruning. Cold tolerance has been observed to USDA Zone 7B. In container culture, plants are observed to have a superior shelf-life. The new plant is a *Rhaphiolepis*, typically useful as a landscape plant.

3 Drawing Sheets

Latin name of the genus and species: *Rhaphiolepis indica.*
Variety denomination: 'DB-01'.

BACKGROUND OF THE INVENTION

The present invention relates to a new and distinct variety of evergreen perennial *Rhaphiolepis indica*, which has been named 'DB-01'. *Rhaphiolepis indica* is a medium sized shrub that is used as an ornamental plant in landscape and amenity horticulture. Short, compact forms of *Rhaphiolepis indica* have been selected previously for use in landscape and ornamental horticulture.

The cultivar 'DB-01' was discovered in April 2007 in a group of seedlings resulting from an open pollination of unidentified *Rhaphiolepis indica* parents in Semmes, Ala.

The new variety 'DB-01' was first asexually propagated by vegetative cuttings at a nursery in Semmes, Ala. in December 2013. Subsequent asexual propagation has shown the features of the new variety are stable and reproduced true to type.

SUMMARY OF THE INVENTION

The cultivar 'DB-01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DB-01'. These characteristics in combination distinguish 'DB-01' as a new and distinct *Rhaphiolepis* cultivar:

1. Very compact and mounding nearly prostrate form.
2. Never requires pruning in container culture or in the landscape.
3. Unique branching structure (a factor in its lateral growth is the emergence of elongated branching).

4. Grows wider than tall.
5. Drought tolerant.
6. Hardy through zone 7B.
7. Minimal blooming while in container culture; resulting in less susceptibility to fire blight.
8. Superior shelf life in container.

PARENT COMPARISON

The parent varieties are unknown.

COMMERCIAL COMPARISON

'DB-01' can be compared to the *Rhaphiolepis* variety 'Georgia Petite', U.S. Plant Pat. No. 9,983. Plants of the new cultivar 'DB-01' are similar to plants of 'Georgia Petite' in most horticultural characteristics, however, plants of the new cultivar 'DB-01' differ in the following:

1. This comparator requires pruning to attain fullness, while the new variety does not require pruning.
2. This comparator is not as cold hardy as the new variety.
3. This comparator is not as drought tolerant as the new variety.
5. This comparator is not as wide as the new variety.

'DB-01' can also be compared to the *Rhaphiolepis* variety 'Snow White', unpatented. Plants of the new cultivar 'DB-01' are similar to plants of 'Snow White' in most horticultural characteristics, however, plants of the new cultivar 'DB-01' differ in the following:

1. Flowers of this comparator are single and white, while flowers of the new variety are white, flushed with pink at first opening.
2. This comparator blooms abundantly in container culture and landscape, while the new variety blooms minimally.
3. This comparator is taller and wider than the new variety.

4. This comparator requires pruning to attain fullness, while the new variety does not require pruning.
5. This comparator is not as hardy as the new variety.

p BRIEF DESCRIPTION OF THE PHOTOGRAPHS

The accompanying photograph in FIG. 1 illustrates a typical plant of 'DB-01' grown outdoors during Spring.

Figure 1:
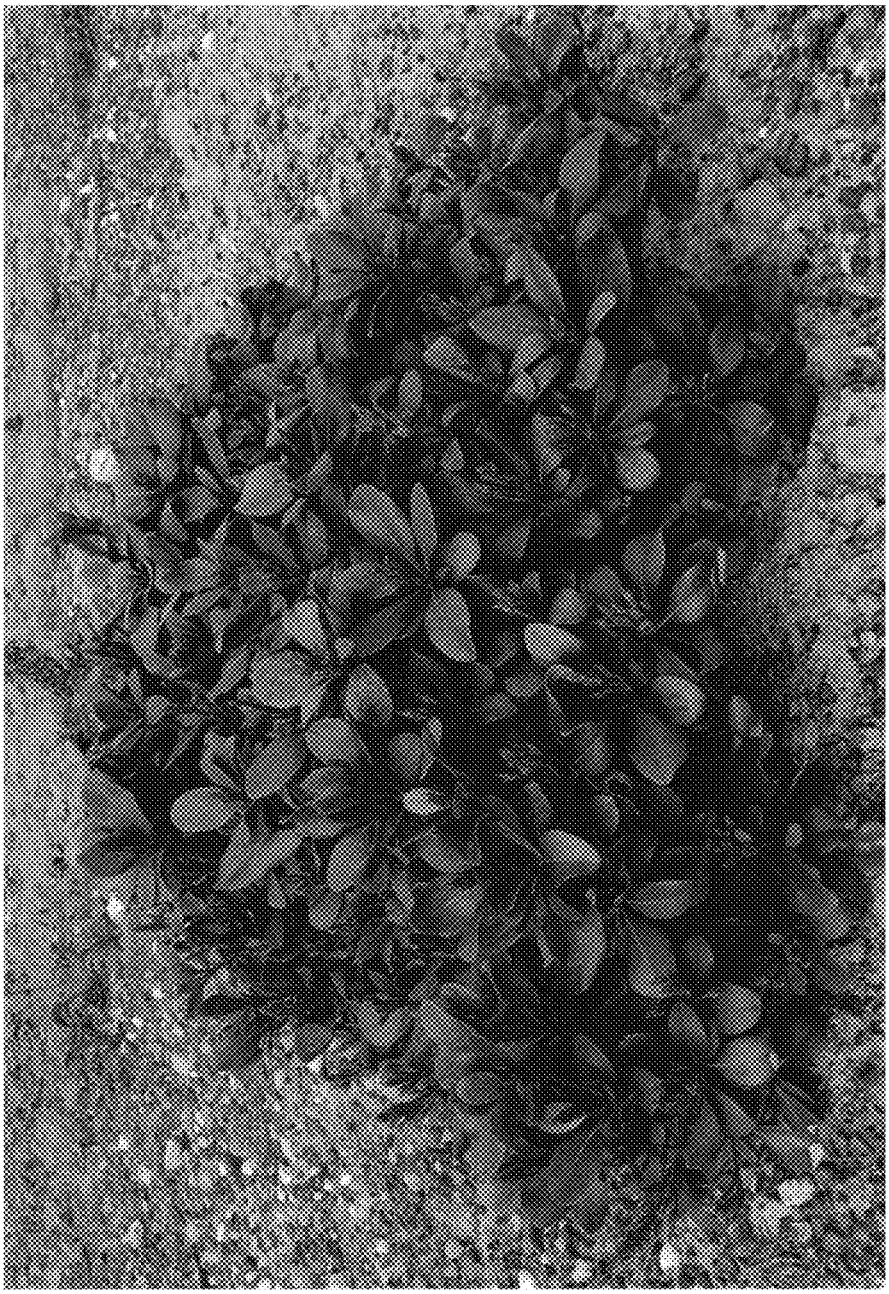
Figure 2:
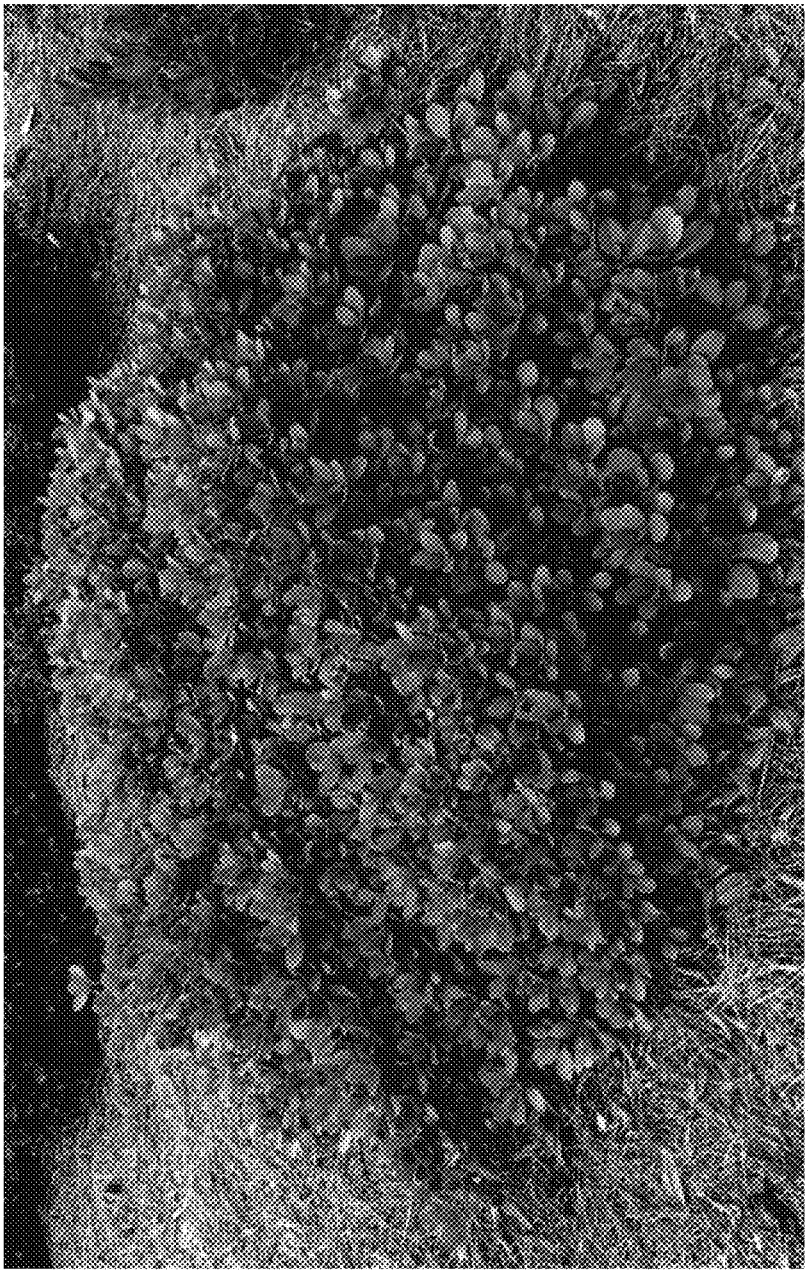
FIG. 2 illustrates a plant of 'DB-01' during Summer.
Figure 3:
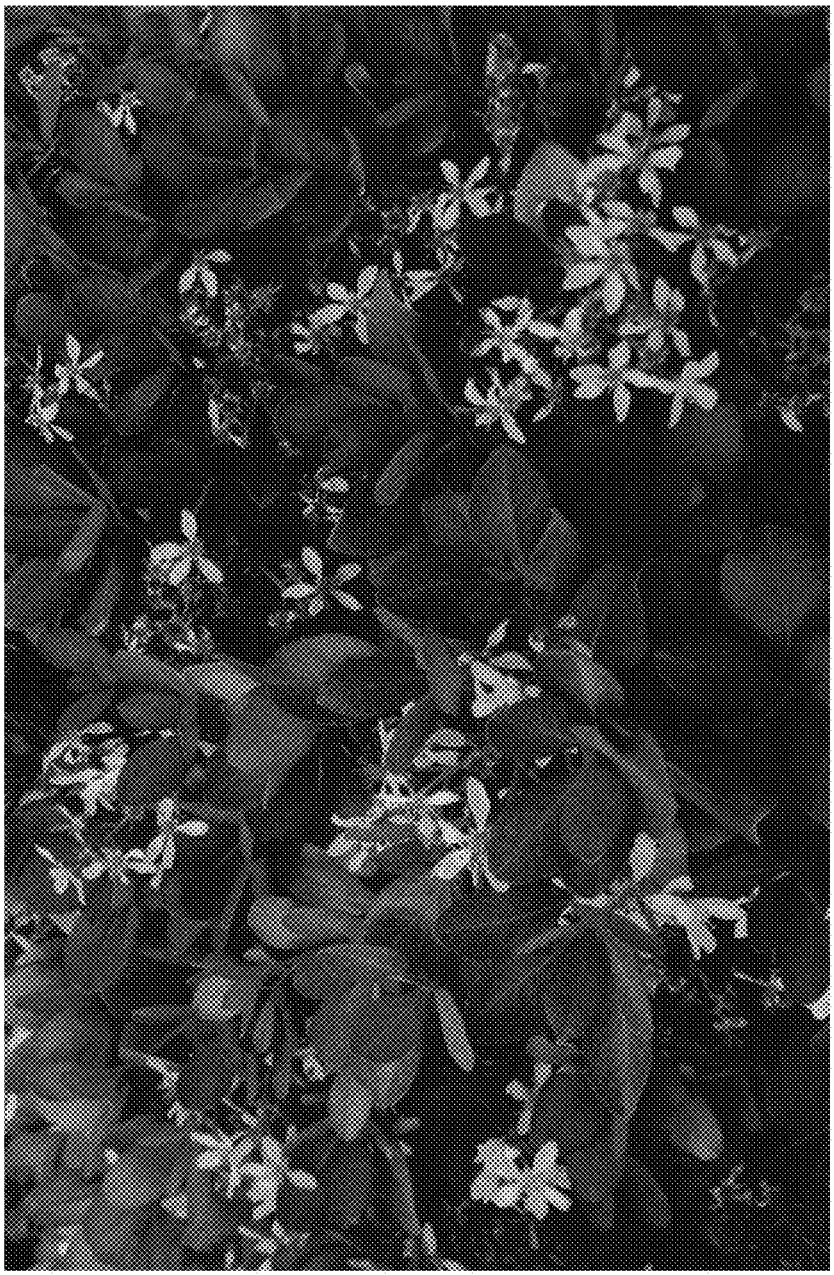
FIG. 3 illustrates in full color a close up of typical flowers and new growth of the new variety.

The plant in all Figures is approximately 2 years old and is shown planted in the ground. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'DB-01' plants grown outdoors in Loxley, Ala. Plants are approximately 3 years old, in a 3 gallon nursery container. Measurements and numerical values represent averages of typical plant types.

Botanical classification: *Rhaphiolepis indica* 'DB-01'.

PROPAGATION

Propagation method: Typically by semi-hardwood cuttings in Spring and Summer.

Root description: Fine, fibrous young roots, well branched. Colored near RHS Grey-Brown 199A.

PLANT

Growth habit: Compact , globular shrub.

Height: Approximately 24 cm to top of foliar plane. 32 cm to top of flowering plane.

Plant spread: Approximately 54 cm.

Branching characteristics: Very well branched, approximately 6 primary branches from the center of the plant. Branches occur at approximately 45° to 75° angles. Each primary branch has 4 to 8 lateral branches.

Primary branches:

Length of primary branches: Average 12 to 28 cm.

Diameter of primary branches: Average range 4 to 7 mm.

Primary branch strength: Very strong, difficult to break.

Primary branch color: Young primary branches near RHS Green 143C. Mature branches woody, colored near Greyed-Green 197C.

Primary branch texture: Immature growth very slightly hirsute. Older growth scaly.

Lateral branches:

Number of lateral branches: Approximately 4 to 8 per primary branch.

Length of lateral branches: Average range 4 to 8 cm.

Diameter of lateral branches: Average 4 mm.

Lateral branch strength: Strong.

Lateral branch color: Young primary branches near RHS Green 143C. Mature branches woody, colored near RHS Greyed-Green 197C.

Lateral branch texture: Immature growth very slightly hirsute. Older growth scaly.

Internode length: Average 5 mm.

Age of plant described: Approximately 2 years.

FOLIAGE

Leaf:

*Type*.—Simple.

*Arrangement*.—Whorled.

*Average length*.—Approximately 6.5 cm.

*Average width*.—Approximately 2.8 cm.

*Shape of blade*.—Elliptic.

*Apex*.—Broad acute with single serration.

*Base*.—Broad attenuate.

*Attachment*.—Stalked.

*Margin*.—Serrate.

*Texture of top surface*.—Pubescent. Hairs appressed.

*Texture of bottom surface*.—Glabrous.

*Color*.—Newest foliage upper side: Near RHS Greyed-Red 179A and 182A. Newest foliage under side: Near RHS Greyed-Red 182A. Young foliage upper side: Near RHS Green 137D. Young foliage under side: Near RHS Green 137D. Mature foliage upper side: Near RHS Green 139A. Mature foliage under side: Near RHS Green 137D.

*Venation*.—Type: Pinnate. Venation color upper side: Near RHS Yellow-Green N144A. Venation color under side: Near RHS Green 138B.

Petiole:

*Length*.—About 0.6 cm.

*Diameter*.—About 0.15 cm.

*Color*.—Upper Surface: Near RHS Green 137C. Lower Surface: Near RHS Yellow-Green 144A.

FLOWER

Bloom period: Early Spring until late Spring, early Summer.

Inflorescence: Panicle composed of 4 to 6 racemes. Each raceme has 4 to 8 flowers.

Panicle:

*Height*.—Average 9.0 cm.

*Diameter*.—Average 11.0 cm.

Raceme:

*Height*.—Average 3 to 4 cm. Excluding peduncle.

*Diameter*.—Average 2.0 to 3.0 cm.

Panicle peduncle:

*Length*.—Average 2 to 3 cm.

*Diameter*.—3 mm.

*Color*.—Near RHS Yellow-Green 144C.

*Texture*.—Glabrous to very slightly hirsute.

*Aspect*.—Straight. Angle of attachment, upright, approximately 0 to 15° angle from stem.

Raceme peduncle:

*Length*.—Average 3.5 to 4.5 cm.

*Diameter*.—2 to 3 mm.

*Color*.—Near RHS Yellow-Green N144D.

*Texture*.—Glabrous.

*Aspect*.—Straight. Angle of attachment approximately 45° angle from peduncle.

Raceme pedicel:

*Length*.—Average 1.0 to 1.5 cm.

*Diameter*.—2 to 3 mm.

*Color*.—Near RHS Yellow-Green N144D.

*Texture*.—Glabrous.

*Aspect*.—Straight. Angle of attachment approximately 45° angle from peduncle.

Flowers:

*Length*.—Average 1.5 cm.

*Diameter*.—Average 8 mm.

*Facing direction*.—Upwardly facing.

*Fragrance*.—Very faint earthy scent.

Petals:

*Petal number*.—5.

*Arrangement*.—Radial, not overlapping.

*Length*.—Approximately 1.0 cm.

*Width*.—Approximately 5 mm.

*Apex*.—Rounded.

*Base*.—Attenuate.

*Shape*.—Broad elliptic.

*Petal margin*.—Entire.

*Petal texture*.—Smooth, all surfaces.

*Color*.—Upper surface at first opening: Near RHS White N155C, flushed Red 36D. Under surface at first opening: Near RHS White N155C, flushed Red 49D. Upper surface at maturity: Near RHS White 155D. Under surface at maturity: Near RHS White N155C. Upper surface at fading: Near RHS White N155B. Under surface at fading: Near RHS White N155B.

Bud:

*Shape*.—Elliptic.

*Length*.—1.3 cm.

*Diameter*.—4 mm.

*Color*.—Near RHS Red 36D.

Calyx/sepals:

*Quantity per flower*.—5 sepals.

*Shape*.—Narrow deltate.

*Length*.—3 to 6 mm.

*Width*.—2 to 3 mm.

*Apex*.—Acute.

*Base*.—Fused.

*Margin*.—Entire.

*Texture*.—Glabrous.

*Color*.—Inner Surface: Near RHS Yellow-Green N144A. Outer Surface: Near RHS Yellow-Green 144B.

Floral bract: 2 bracts subtending each individual flower. Sub-opposite. Drying and falling off with floral maturity.

*Shape*.—Strap shaped.

*Length*.—4 to 7 mm.

*Width*.—2 mm.

*Apex*.—Acute.

*Base*.—Truncate.

*Margin*.—Entire.

*Texture*.—Glabrous, papery.

*Color*.—Inner Surface: Near RHS Yellow-Green 153B. Outer Surface: Near RHS Yellow-Green 153B.

REPRODUCTIVE ORGANS

Stamens:

*Number*.—10.

*Length*.—5 to 10 mm.

*Width*.—1 mm.

*Color*.—Near RHS Red 36C.

Anthers:

*Length*.—Approximately 2 mm.

*Color*.—Near RHS Greyed-Purple 187B.

*Pollen*.—Scant, colored near RHS Greyed-Purple 183D.

Pistil:

*Number*.—1.

*Length*.—1.5 cm.

*Style*.—2 styles.

*Style length*.—Average 1.2 cm.

*Color*.—Near RHS Red 53D.

*Stigma*.—Linear, colored near Red 36D.

*Ovary*.—Ovate, approximately 3 mm in length and 2 mm in diameter. Colored near RHS Yellow-Green 145A.

OTHER CHARACTERISTICS

Disease and pest resistance: Not observed to be susceptible nor resistant to normal diseases and pests of *Rhaphiolepis*.

Temperature tolerance: Low temperature tolerance to at least USDA Zone 7B. High temperature tolerance observed to at least 38° C.

Drought tolerance: Good tolerance for drought, especially once established.

Fruit/seed production: Not observed to date.

What is claimed is:

1. A new and distinct cultivar of *Rhaphiolepis indica* plant named 'DB-01', substantially as described and illustrated herein.

* * * * *